(12) United States Patent
Quan et al.

(10) Patent No.: US 10,589,006 B2
(45) Date of Patent: Mar. 17, 2020

(54) MICRONEEDLE AND METHOD FOR PRODUCING SAME

(71) Applicant: COSMED PHARMACEUTICAL CO., LTD., Kyoto, Kyoto (JP)

(72) Inventors: Ying-shu Quan, Kyoto (JP); Ying-zhe Li, Kyoto (JP); Mio Saito, Kyoto (JP); Shouta Kitaoka, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 15/560,142

(22) PCT Filed: Dec. 10, 2015

(86) PCT No.: PCT/JP2015/084690
§ 371 (c)(1),
(2) Date: Sep. 20, 2017

(87) PCT Pub. No.: WO2016/151961
PCT Pub. Date: Sep. 29, 2016

(65) Prior Publication Data
US 2018/0078680 A1 Mar. 22, 2018

(30) Foreign Application Priority Data
Mar. 23, 2015 (JP) .................................. 2015-080388

(51) Int. Cl.
*A61L 31/06* (2006.01)
*A61M 37/00* (2006.01)
(Continued)

(52) U.S. Cl.
CPC ............ *A61L 31/06* (2013.01); *A61K 9/0021* (2013.01); *A61L 31/16* (2013.01); *A61M 37/00* (2013.01);
(Continued)

(58) Field of Classification Search
CPC ........................................................ A61L 31/06
See application file for complete search history.

(56) References Cited

U.S. PATENT DOCUMENTS

2008/0221532 A1 9/2008 Ogawa
2010/0004608 A1 1/2010 Hamamoto et al.
(Continued)

FOREIGN PATENT DOCUMENTS

CN 102395354 A 3/2012
CN 104321105 A 1/2015
(Continued)

OTHER PUBLICATIONS

McAlliseter et al (PNAS, 2003, vol. 100, No. 24, 13755-13760) (Year: 2003).*
(Continued)

*Primary Examiner* — Benjamin J Packard
(74) *Attorney, Agent, or Firm* — Cheng Law Group, PLLC

(57) ABSTRACT

Provided are a microneedle with excellent performance and a method for manufacturing the microneedle.
A microneedle array in which a polyglycolic acid is used as a material, crystallinity of the polyglycolic acid is 21% or more and axial contraction rate of tips is 99% or more, and a manufacturing method in which a polyglycolic acid are injection-molded at a cylinder temperature of 230-280° C., a metal mold temperature of 60-130° C., and an injection pressure of 1000-1500 KPa so as to manufacture a microneedle array in which crystallinity of the polyglycolic acid is 21% or more and an axial contraction rate of tips is 99% or more.

10 Claims, 4 Drawing Sheets

(51) Int. Cl.
*A61K 9/00* (2006.01)
*A61L 31/16* (2006.01)
*B29C 45/00* (2006.01)
B29K 67/00 (2006.01)
B29L 31/00 (2006.01)

(52) U.S. Cl.
CPC ..... *A61M 37/0015* (2013.01); *B29C 45/0001* (2013.01); *A61M 2037/0023* (2013.01); *A61M 2037/0053* (2013.01); *B29K 2067/043* (2013.01); *B29K 2905/00* (2013.01); *B29L 2031/7544* (2013.01)

(56) References Cited

U.S. PATENT DOCUMENTS

| | | |
|---|---|---|
| 2011/0152792 A1 | 6/2011 | Takada |
| 2012/0136312 A1 | 5/2012 | Terahara et al. |
| 2013/0296790 A1 | 11/2013 | Masaoka et al. |
| 2014/0066842 A1 | 3/2014 | Zhang et al. |
| 2014/0276589 A1 | 9/2014 | Bayramov et al. |
| 2015/0094648 A1 | 4/2015 | Toyohara et al. |
| 2016/0001053 A1 | 1/2016 | Quan et al. |

FOREIGN PATENT DOCUMENTS

| | | |
|---|---|---|
| EP | 2 457 592 A1 | 5/2012 |
| EP | 2 842 595 A1 | 3/2015 |
| JP | 2008-142183 A | 6/2008 |
| JP | 2008-260902 A | 10/2008 |
| JP | 2010-56400 A | 3/2010 |
| JP | 2010-82401 A | 4/2010 |
| JP | 2010-247535 A | 11/2010 |
| JP | 2012-143423 A | 8/2012 |
| JP | 5050130 B2 | 10/2012 |
| JP | 2013-112671 A | 6/2013 |
| JP | 2014-79557 A | 5/2014 |
| JP | 2014-151122 A | 8/2014 |
| JP | 5620911 B2 | 11/2014 |
| WO | WO-2008/093679 A1 | 8/2008 |
| WO | WO-2010/016218 A1 | 2/2010 |
| WO | WO-2012/057345 A1 | 5/2012 |
| WO | WO-2014/126052 A1 | 8/2014 |

OTHER PUBLICATIONS

Tian et al ((2008) Materials and microfabrication processes for microfluidic devices. In Microfluidics for Biological Applications, pp. 35-92) (Year: 2008).*
Park et al (Biomed Microdevices (2007) 9:223-234) (Year: 2007).*
Supplementary European Search Report for the Application No. EP 15 886 513.9 dated Oct. 10, 2018.
Boehm, Ryan et al., "Polyglycolic acid microneedles modified with inkjet-deposited antifungal coatings", Biointerphases, 2015, vol. 10, No. 1, pp. 011004-1 to 011004-10 (XP055510304, US, ISSN: 1934-8630, DOI: 10.1116/1.4913378).
International Search Report for the Application No. PCT/JP2015/084690 dated Jan. 26, 2016.
Written Opinion of the International Searching Authority (PCT/ISA/237) for Application No. PCT/JP2015/084690 dated Jan. 26, 2016.
Davis, Shawn P. et al., "Insertion of microneedles into skin: measurement and prediction of insertion force and needle fracture force", Journal of Biomechanics, 2004, vol. 37, pp. 1155-1163.
Written Opinion of the International Searching Authority (PCT/ISA/237) for Application No. PCT/JP2015/084690 dated Jan. 26, 2016 (English Translation dated Oct. 5, 2017).
The First Office Action for the Application No. 201580078126.3 from The State Intellectual Property Office of the People's Republic of China dated Dec. 11, 2019.

* cited by examiner

[FIG. 1]
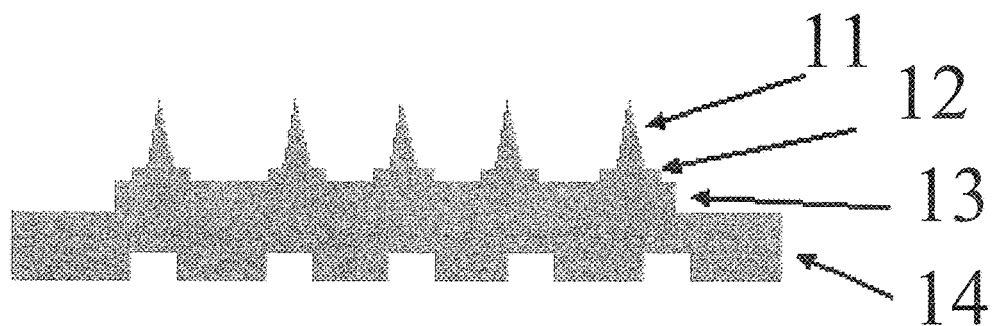
[FIG. 2]
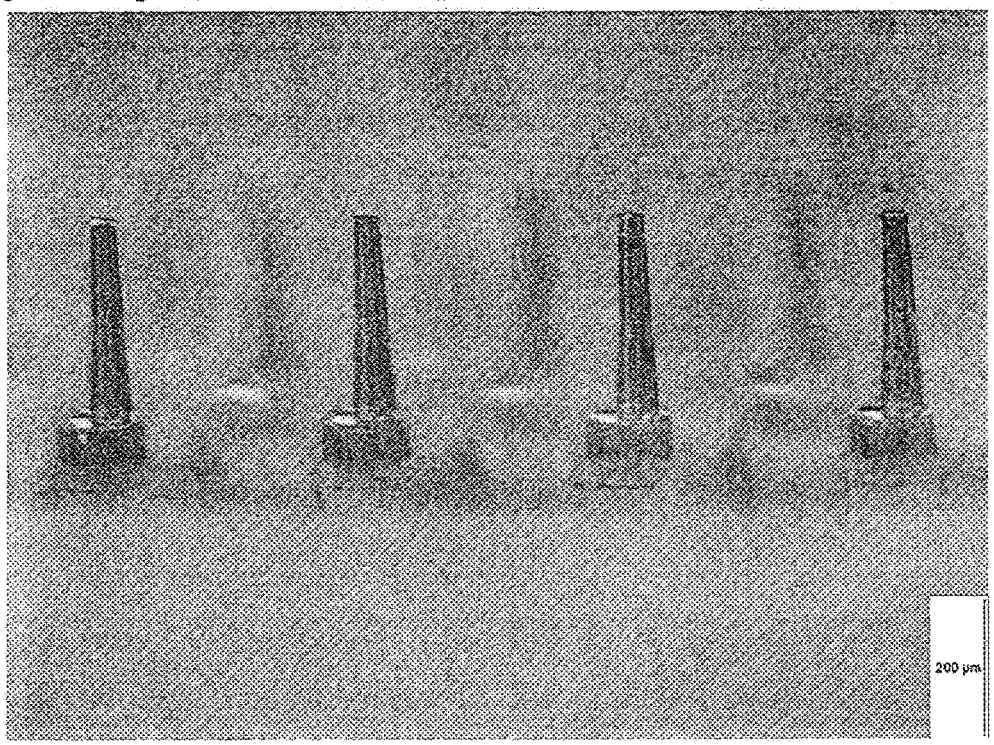
[FIG. 3]
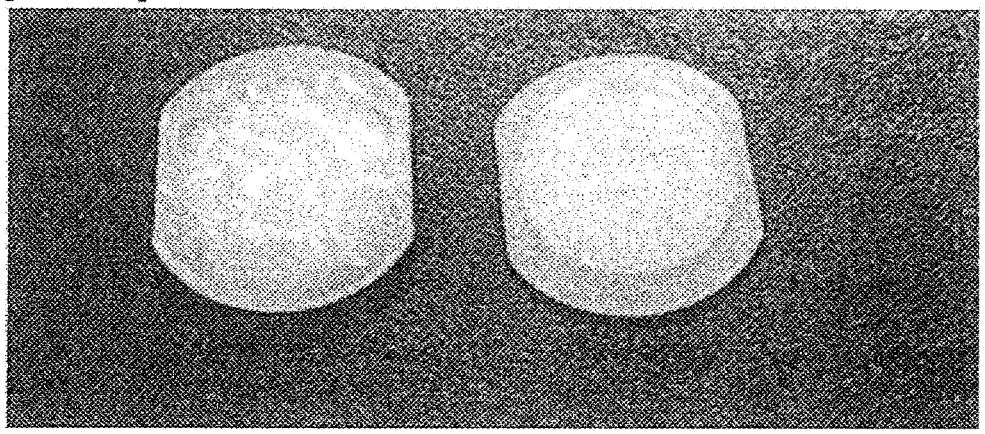

[FIG. 4]
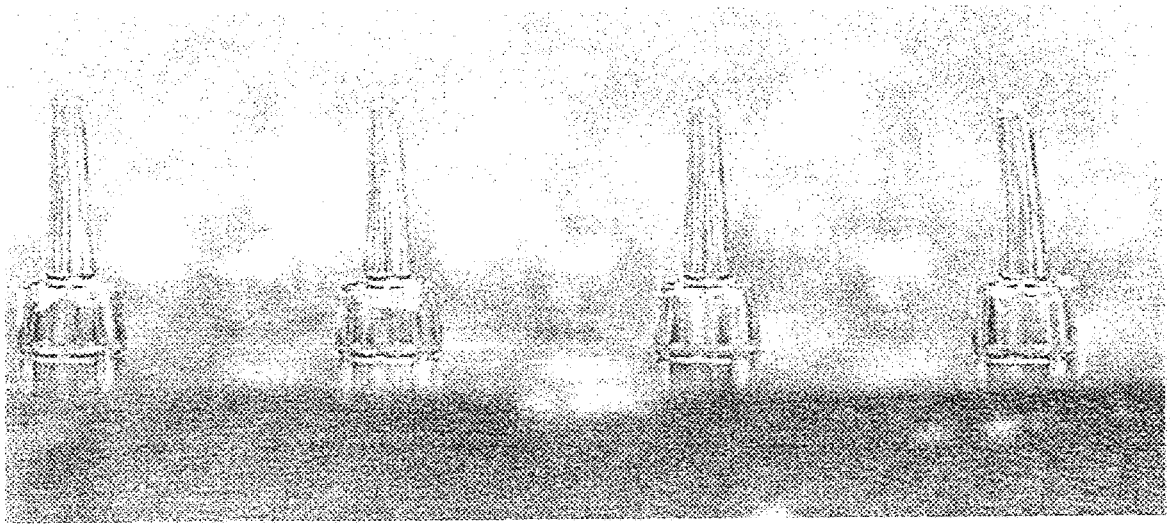
[FIG. 5]
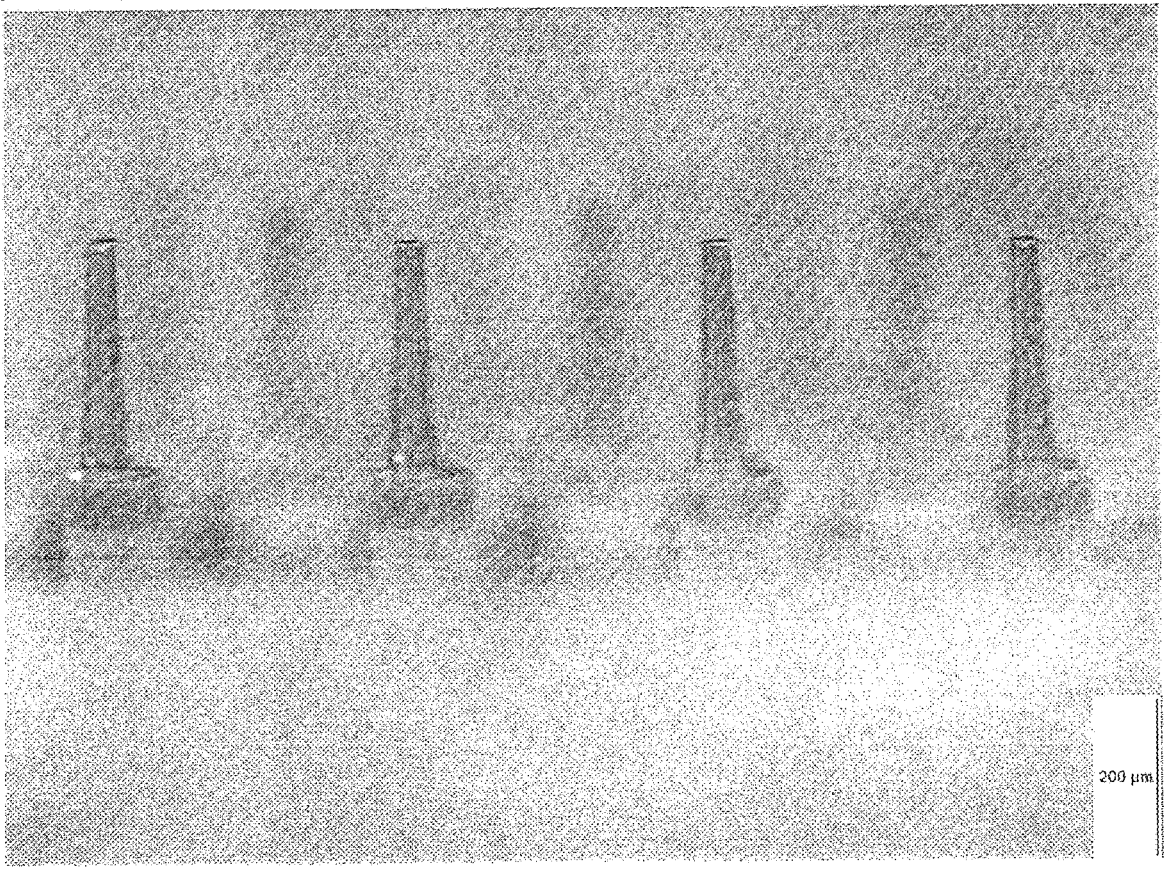

[FIG. 6]
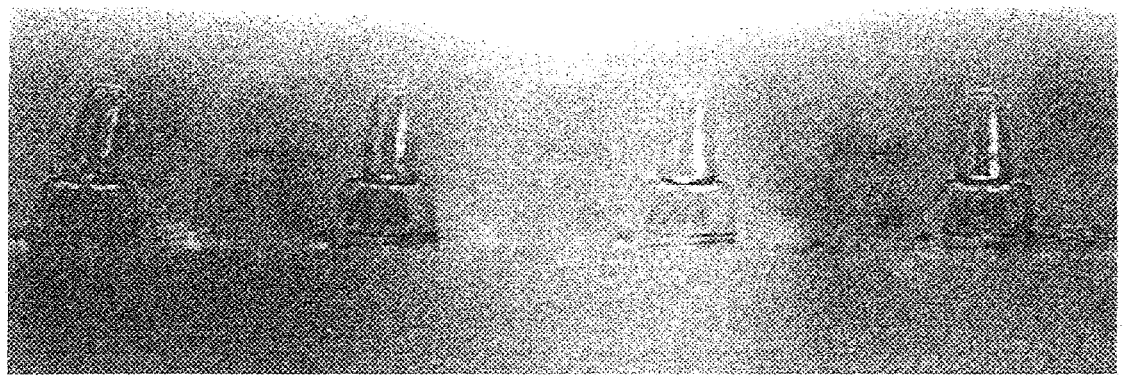
[FIG. 7]
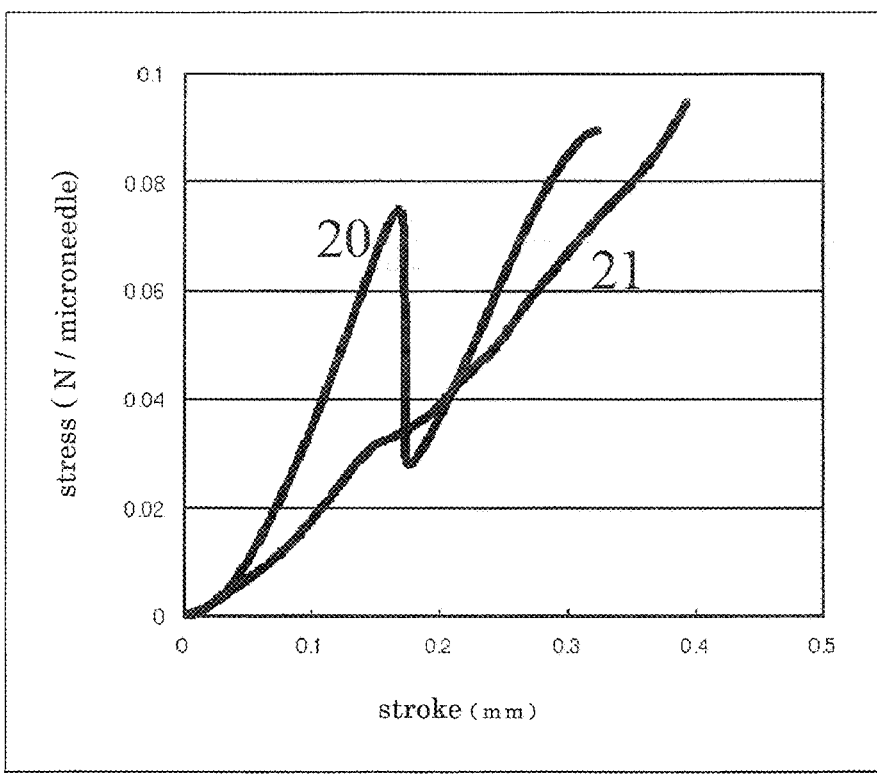
[FIG. 8]
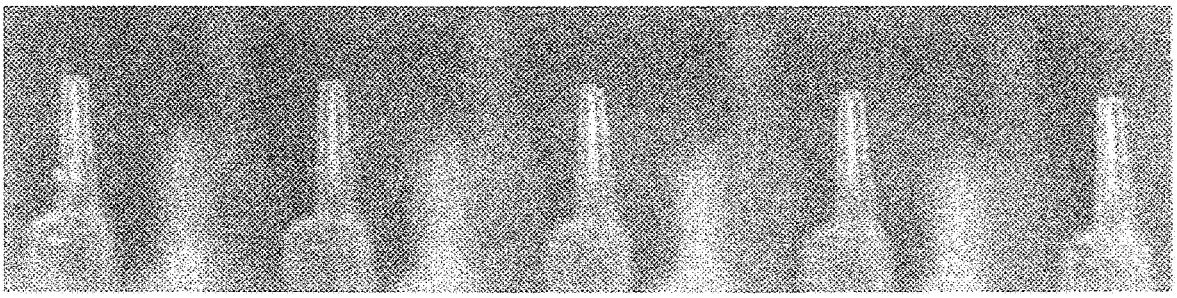

[FIG. 9]
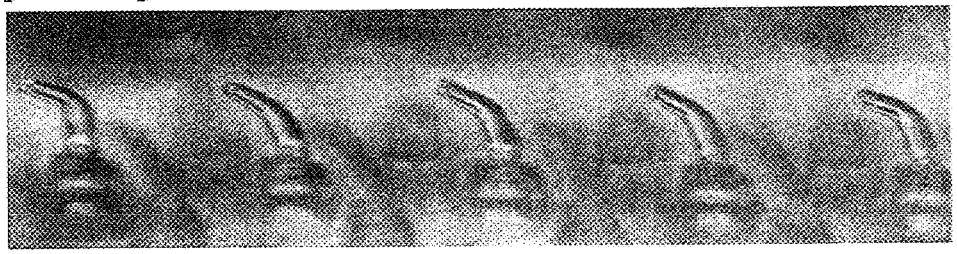
[FIG. 10]
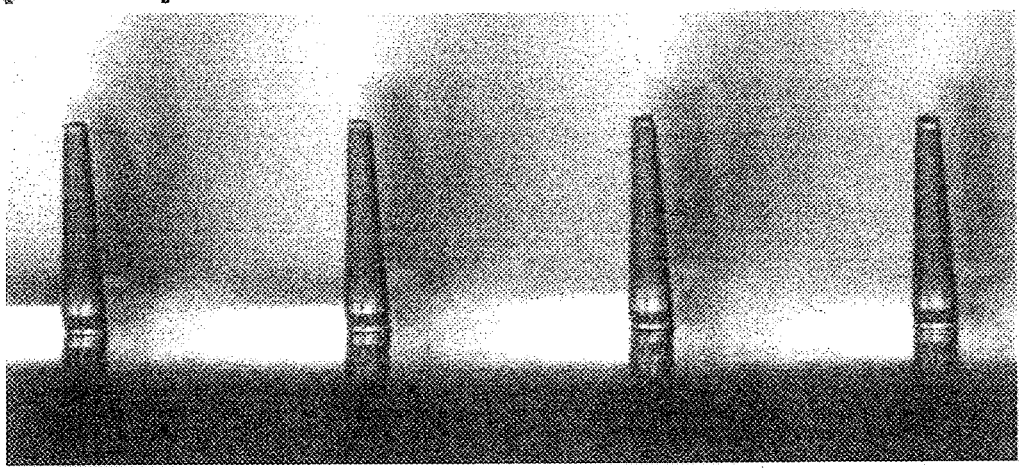
[FIG. 11]
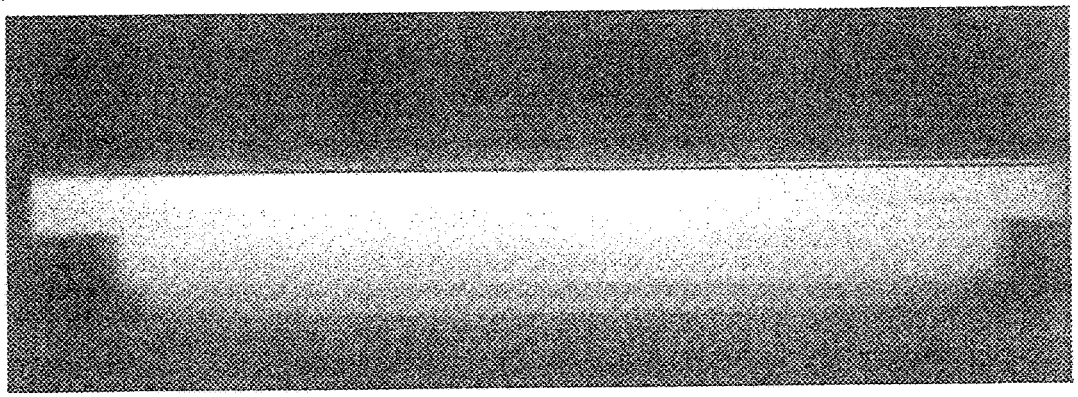
[FIG. 12]
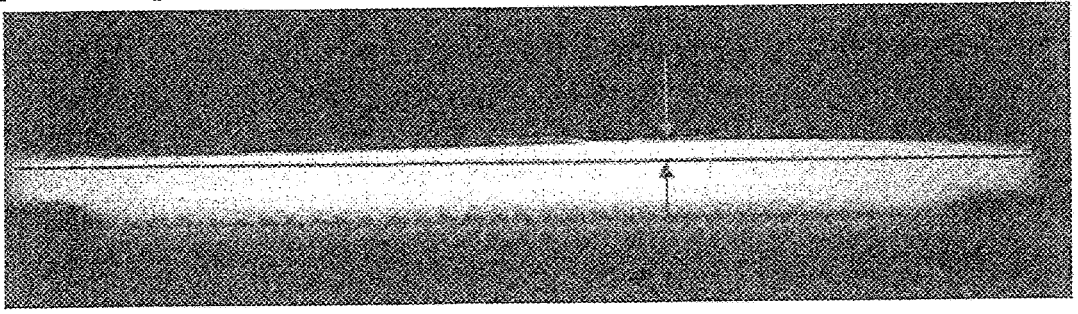

US 10,589,006 B2

MICRONEEDLE AND METHOD FOR PRODUCING SAME

TECHNICAL FIELD

The present invention relates to microneedles of polyglycolic acid (PGA), polylactic acid (PLA), and a copolymer thereof made by an injection molding method; and a manufacturing method thereof.

BACKGROUND ART

In transdermal administration of a drug, stratum corneum works as a barrier to drug permeation, so the drug cannot sufficiently penetrate only by applying the drug on a skin surface. In contrast, perforation of corneum by using a minute needle, i.e. a microneedle can remarkably improve drug permeation efficiency compared to the application method. An article in which a large number of the microneedles are integrated on a substrate is a microneedle array. In addition, a product in which an adhesive tape for adhering the microneedle array to a skin and a cover sheet for maintaining an aseptic state until its use, etc. are added to the microneedle array in order to facilitate its use is called a microneedle patch. "Tape" as used herein means a film, or a fabric or a paper to which an adhesive agent is applied.

Manufacturing methods of the microneedles are greatly different whether a material of the microneedles is metal or resin, and various manufacturing methods have been currently tried and reported. Since the microneedles made of resin are easy to process and thus microneedles in various shapes can be made, much examination has been conducted. For example, a method in which a flat plate made of resin is molten with heating styli and stretch formed (Patent Document 1, 2); a method in which an aqueous solution of a water-soluble polymer is injected into a mold, and then dried and solidified to make the microneedles (Patent Document 3, 4); a manufacturing method in which polyglycolic acid in a molten state is compressed in a microneedle mold by pressing, and then solidified at low temperature (Patent Document 5), and a manufacturing method in which polyglycolic acid is injection-molded (Patent Document 6); etc. have been reported.

"Injection molding method" is a known method in which thermoplastic resin or the like is molten at high temperature and then high-pressure injected into a low temperature metal mold to solidify the resin. The resin used for injection-molding can include a general-purpose resin such as polyethylene resin, polypropylene resin, polyamide resin, and an engineering plastic such as polycarbonate resin, modified polyphenylene ether resin, polybutylene terephthalate resin, polyethylene terephthalate resin. Considering the worst case where the resin remains in a living body, as the thermoplastic resin suitable for the microneedle, a safety-guaranteed biodegradable resin such as polyglycolic acid resin, polylactic acid, and a copolymer thereof is preferable to a non-biodegradable resin such as polybutylene terephthalate resin.

When crystallinity is enhanced by adjusting an injection molding condition, strength of polyglycolic acid can be enhanced (Patent Document 7). In order to obtain polyglycolic acid with crystallinity of 5% or more, the resin should be injection-molded in a relatively high temperature condition where a resin temperature is 230-270° C. and a metal mold temperature is 80-130° C. (Patent Document 8). These polyglycolic acid molded articles are goods for consumer industrial application and relation between physical properties and crystallizability in the microneedle is not suggested, so it has been unexpected whether the physical properties of the microneedle are completely changed by crystallization in molding.

Furthermore, there is not currently a document in which correlation between the molding condition (especially the metal mold temperature) and the physical properties of the microneedle when the microneedles are manufactured by the injection molding method is examined based on experienced knowledge "Compressive strength per one needle should be 0.056 N or more to penetrate a skin" (Non-Patent Document 1). In particular, there is not a report in which a condition for manufacturing microneedles with a sharp tip by the injection molding method using polyglycolic acid, polylactic acid, and a copolymer thereof as the material is examined in detail.

PRIOR ART DOCUMENTS

Patent Documents

[Patent Document 1] WO 2008/093679 (Re-publication, MEDRx Co., Ltd)
[Patent Document 2] WO 2010/016218 (Re-publication, Kagawa University)
[Patent Document 3] JP 2008-142183 A (Fujifilm Corporation)
[Patent Document 4] JP 2010-082401 A (CosMED Pharmaceutical Co. Ltd)
[Patent Document 5] WO 2012-057345 (TEIJIN LIMITED)
[Patent Document 6] JP 2014-079557 A (CosMED Pharmaceutical Co. Ltd, Step)
[Patent Document 7] JP 2008-260902 A (KUREHA CORPORATION)
[Patent Document 8] JP 2010-056400 A (Tokyo University)

Non-Patent Document

[Non-Patent Document 1] S. P. Davis et al., Journal of Biomechanics, Elsevier, 2004, Vol. 37, p 1155-1163

SUMMARY OF INVENTION

Technical Problem

An object of the present invention is to provide a manufacturing method of microneedles with excellent performance by examining association between crystallinity of the microneedles and physical properties of a material or the manufacturing method so that microneedles with a sharp tip are manufactured by the injection molding method.

Solution to Problem

A manufacturing method of microneedles by the injection molding method according to the present invention made for achieving the object is characterized in that a material is polyglycolic acid, polylactic acid, or a copolymer of polyglycolic acid and polylactic acid, or a mixture thereof; that the microneedles are manufactured by the injection molding method, that crystallinity of the microneedles is 21% or more, and that an axial contraction rate of tips is 99% or more.

When pellets consisting of a thermoplastic resin material mainly composed of polyglycolic acid are supplied to an injection molding machine equipped with a metal mold for injection-molding microneedles, and then injection-molded at a cylinder temperature of 230-280° C., a metal mold temperature of 60-130° C., and an injection pressure of 1000-1500 KPa, the crystallinity can be 20% or more. The present invention is characterized in that the injection pressure is 1000-1500 KPa and that the metal mold temperature is 60-130° C., so crystallization proceeds by injection-molding in such a condition and thus microneedles with excellent physical properties which do not change with time can be obtained.

As the thermoplastic resin material, polyglycolic acid, polylactic acid or a copolymer thereof can be used either alone or as a mixture. Furthermore, a composition in which an inorganic filler, another thermoplastic resin, and the like are blended can be used within a range where the object of the present invention is not inhibited.

Specifically, a composition (compound) in which 0-20 pts. wt. of the inorganic filler, 0-30 pts. wt. of the other thermoplastic resin, and the like are blended with 100 pts. wt. of polyglycolic acid can be used. If the ratio of the inorganic filler or the other thermoplastic resin exceeds 20 pts. wt., impact strength and toughness of an obtained injection-molded article are insufficient and melt processability may be also reduced. The inorganic filler includes silica, titanium oxide, calcium carbonate, and calcium silicate, etc. These inorganic fillers can be used either alone respectively or in combination with two or more kinds thereof.

The other thermoplastic resin includes a homopolymer and a copolymer of ε-caprolactone, and TPX, etc. These thermoplastic resins can be used either alone respectively or in combination with two or more kinds thereof. The other thermoplastic resin is generally used in the ratio of 0-30 pts. wt. to 100 pts. wt. of the polyglycolic acid.

When the crystallinity of the polyglycolic acid is set to 21% or more using the suitable injection molding condition as defined herein, the microneedle having a long needle and strong compressive stress can be obtained by fitting it well into a cavity. When these microneedles are compressed, a clear yield point is observed.
In contrast, when the crystallization is insufficient, the clear yield point is not observed, microneedles are bent little by little, and a Young's modulus is also small.
Compressive strength per one microneedle at the yield point is about 0.070 N. Such a microneedle injection-molded article made of neat resin with the high compressive strength is not seen in the conventional injection-molded microneedles. If the polyglycolic acid is used as the raw material under an injection molding condition unsuitable for crystallization, a needle shape of an injection-molded article is uneven, density and compressive strength are also low as shown in Examples and Comparative Examples.

By optimizing the injection molding condition of the polyglycolic acid to enhance the crystallinity, the needles become thin and long as not found in the conventional goods, so extremely hard and viscous microneedles can be obtained. When character of the microneedles is taken into consideration, it is extremely important that the crystallization and the compressive strength are enhanced.

Since the compressive strength per one needle of the polyglycolic acid microneedles with high crystallinity is approximately 0.07 N, which exceeds 0.056 N (Non-Patent Document 1), the microneedles can be surely inserted into a skin. In contrast, if the crystallinity is low, the clear yield point may not be often observed. Even if a yield point is observed, the compressive strength per one needle is 0.03-0.05 N, i.e. strength at which microneedles might not be inserted into a skin.

The polyglycolic acid microneedles with enhanced crystallinity have an important characteristic in that shape change with time is extremely small. If the crystallinity is low, crystallization gradually proceeds during room temperature preservation, and thereby a height of the needles is reduced and a base portion is also contracted and deformed. In contrast, if the polyglycolic acid is crystallized in molding, such deformation does not occur at all, and thus the deformation of the needles during preservation does not occur. This is a prominent characteristic of the microneedles according to the present invention. There is a report in which, in order to enhance the crystallinity of a polyglycolic acid molded article, the polyglycolic acid is molded in an amorphous state or a low crystallized state and then crystallization is promoted by exposing to high temperature (heat treatment) to obtain the crystallized molded article (Patent Document 8). However, this method cannot be used for microneedle molding. This is because, if microneedles injection-molded in an amorphous state are heat-treated, the needles are bent and remarkably short, so they are unavailable.

For actually making the microneedles with the crystallinity enhanced by the injection molding method, it is important that the metal mold temperature and the injection pressure are adjusted. The present invention is characterized in that excellent microneedles can be obtained by setting the injection pressure to 1000-1500 KPa and the metal mold temperature to 60-130° C. Since the microneedles are small compared to the other molded articles, they are cooled to the metal mold temperature immediately, so cycle time of the injection molding can be short, i.e. for 10-30 seconds.

The microneedles may be shaped as straight needles without a step thereon, or needles provided with one step, two steps, or three steps thereon. When a length from a substrate to a microneedles tip is defined as a needle height, the needle height is appropriately 0.1-1.5 mm, and more preferably 0.2-0.8 mm. If the needle height is smaller than 0.1 mm, permeation to a skin is difficult. Furthermore, if the needle height is bigger than 1.5 mm, the needles are deeply inserted, so pain, bleeding or the like easily occur. Intervals between the microneedles are suitably 0.2-1.5 mm. If the intervals are narrower than 0.2 mm, density of the microneedles is too dense, so the microneedles are difficult to be inserted to a skin, while, if the intervals are wider than 1.5 mm, the density is too much sparse, so a medicine administration amount per unit area of the microneedle array is small.

Although the microneedles stand in a central part of the substrate, the substrate has optionally a circular, oval, or square shape, etc. Although the microneedle can have a conical, circular truncated cone, quadrangular pyramid, triangular pyramid, or konide-like shape etc., the conical, circular truncated cone, or konide-like shape is the most appropriate when insertion resistance to a skin is considered.

The substrate of the microneedles is not a flat plane but has uneven structure, and preferably has a thickness of 0.3 mm-10 mm. When the substrate has the uneven structure, there are advantages that mechanical strength can be enhanced and that deformation due to aging is little. The uneven structure includes structure with a hole. Although the convex part in the substrate preferably has a height of approximately 0.2-10 mm and the concave part preferably has a depth of 0.2 mm or more, the depth of the concave part in the substrate can be equal to thickness of the substrate at the maximum. A ratio of the substrate concave parts to the entire substrate area is appropriately 10-90%. If the ratio of the concave parts is 10% or less, there is little merit of having the unevenness. Furthermore, if the ratio of the concave parts is 90% or more, the substrate is thin as a whole, so the mechanical strength of the microneedle array may be weakened.

When a drug is held in the microneedles and then delivered into a body, the drug is suitably held only on the tips. "Drug" as used herein means a compound which works on a skin or penetrates a skin to express any beneficial action Examples of a drug suitable for the object of the present invention include bioactive peptides and derivatives thereof, nucleic acids, oligonucleotides, various antigen proteins, bacteria, and virus fragments, etc.

Examples of the above-mentioned bioactive peptides and the derivatives thereof include calcitonin, adrenocorticotropic hormone, parathyroid hormone (PTH), hPTH (1→34), insulin, secretin, oxytocin, angiotensin, β-endorphin, glucagon, vasopressin, somatostatin, gastrin, luteinizing hormone-releasing hormone, enkephalin, neurotensin, atrial natriuretic peptide, growth hormone, growth hormone-releasing hormone, bradykinin, substance P, dynorphin, thyroid stimulating hormone, prolactin, interferons, interleukins, G-CSF, glutathione peroxidase, superoxide dismutase, desmopressin, somatomedin, endothelin, and salts thereof, etc. The antigen proteins include influenza virus antigen, HBs surface antigen, and HBe antigen, etc.

When a solution of the drug is applied to the tips of the microneedles to adhere the drug to the microneedle tips, it is desirable that, in order to enhance adhesion of the drug and to prevent the drug from peeling off in insertion, a coexistent substance is dissolved into the aqueous solution of the drug to adhere the drug to the microneedles with the coexistent substance after application and drying. As the coexistent substance, a substance which does not lose stability of the drug is necessary, and, for example, a water-soluble polymer substance such as hyaluronic acid, collagen, dextrin, dextran, chondroitin, hydroxypropyl cellulose, and ethyl cellulose; low molecular weight saccharides such as glucose, sucrose, maltose, and trehalose; and mixtures thereof are preferable. An antioxidant, a surfactant, and the like may further coexist as required. The solution of the drug is preferably applied to a range of around 500 μm from the tips of the microneedles.

Advantageous Effects of Invention

Microneedles which are manufactured by the injection molding method, using polyglycolic acid, polylactic acid, or a copolymer of polyglycolic acid and polylactic acid, or a mixture thereof as a material, and setting the crystallinity to 21% or more, have strength for being surely inserted into a skin and will not be bent in the insertion of the needles into the skin. Furthermore, the microneedles have biodegradability, so they are safe against an accident, such as breakage. The injection molding method facilitates mass production, so high quality microneedles can be inexpensively provided by this method.

When the microneedles are injection-molded at a metal mold temperature of 60-130° C. and an injection pressure of 1000-1500 KPa using polyglycolic acid as the material, the crystallinity of the obtained microneedles can be 21% or more, so a microneedle array which can be surely inserted and withstand long-term preservation can be obtained.

BRIEF DESCRIPTION OF DRAWINGS

FIG. 1 is a schematic view of a cross-section of a microneedle array.

FIG. 2 is a microscope photograph of microneedles of a microneedle array according to Example 1.

FIG. 3 is a photograph of a front side (right) and a rear side (left) of the microneedle array according to Example 1.

FIG. 4 is a microscope photograph of microneedles of a microneedle array according to Comparative Example 1.

FIG. 5 is a microscope photograph of the microneedle array according to Example 1 after being left at 60° C. for 24 hours.

FIG. 6 is a microscope photograph of the microneedle array according to Comparative Example 1 after being left at 60° C. for 24 hours.

FIG. 7 is a graph showing compression—strain curves of microneedle patches according to Example 1 and Comparative Example 1.

FIG. 8 is a microscope photograph of the microneedles according to Example 1 after skin administration.

FIG. 9 is a microscope photograph of the microneedles according to Comparative Example 1 after skin administration.

FIG. 10 is a microscope photograph of microneedles according to Example 9.

FIG. 11 is a microscope photograph from a transverse direction of the microneedle array according to Example 1 after being left at 40° C. for three months.

FIG. 12 is a microscope photograph from a transverse direction of the microneedle array according to Example 9 after being left at 40° C. for three months.

DESCRIPTION OF EMBODIMENTS

Hereinafter, the embodiments of the present invention will be described in accordance with examples. However, the present invention is not limited to contents of the examples. FIG. 1 schematically shows a cross-sectional view of a microneedle array having typical two stage structure. The microneedles have a tip 11 and a bottom base 12. A substrate 14 has a substrate base stand part 13 and is provided with unevenness.

Polyglycolic acid with (a) melt viscosity η* of 500-1000 Pa·s as measured at a temperature of 250° C. and a shear rate of 100/sec; (b) a melting point Tm of more than 220° C.; and (c) density of approximately 1.5 g/cm$^3$; can be suitably used. For example, polyglycolic acid resin made by KUREHA CORPORATION is suitable. In the following examples and comparative examples, polyglycolic acid (high purity Kuredux: made by KUREHA CORPORATION) was used.

1. Manufacture of Highly Crystallized Microneedles by an Injection Molding Method A metal mold was attached to an injection molding machine (Fanuc Ltd.), and polyglycolic acid was melted to injection-mold. The polyglycolic acid was injection-molded at a cylinder temperature of 235° C., an injection pressure of 1350 KPa, and a metal mold temperature of 120° C., and then a milk-white microneedle array with the cross-sectional shape as shown in FIG. 1 was taken out. FIG. 2 shows a microscope photograph of the microneedles portion of the obtained microneedle array, and FIG. 3 shows a photograph of a front side and a back side of this microneedle array. The total number of the microneedles in the array is 458, and the microneedles have a circular truncated cone shape. This microneedle array is referred to as Example 1.

The microneedles according to Example 1 have the two stage structure as shown in FIG. 1. The microneedles had a bottom base diameter of 0.13 mm, a bottom base height of 0.1 mm, a tip apex diameter of 0.034 mm, a tip base diameter of 0.062 mm, and a tip height of 0.3 mm. Distances between the microneedles were 0.4 mm. A substrate has an oval shape with a major axis of 1.4 mm, a minor axis of 1.2 mm, and a thickness of 1.0 mm, and a substrate base stand part with a thickness of 1.0 mm is provided on the upper part of the substrate. A lower part of the substrate does not have a flat surface but uneven structure and thus has grid-like holes with a depth of 0.5 mm. A total of the bottom base height and the tip height is a needle height of the microneedle.

By variously changing the metal mold temperature, microneedle arrays referred to as Examples 2 to 8 were made in a similar manner to Example 1. Results are summarized in Table 2. However, the microneedles according to Example 8 have one stage structure. "One stage structure" means structure in which microneedles do not have the bottom base and are constituted only with the tip.

2. Manufacture of Lowly Crystallized Microneedles by the Injection Molding Method The metal mold temperature was set to 40-50° C. and then a microneedle array was injection-molded in an almost similar condition to Example 1. FIG. 4 shows a microscope photograph of the obtained microneedles. A tip apex diameter of the obtained microneedles is approximately 0.038 mm, and an almost transparent microneedle array having circular truncated cone shaped microneedles with a tip height of approximately 0.25 mm could be made. This microneedle array is referred to as Comparative Example 1.

By variously changing the cylinder temperature and the metal mold temperature, microneedle arrays referred to as Comparative Example 2 to Comparative Example 4 were made in a similar manner. Results are summarized in Table 2. However, the microneedles according to Comparative Example 4 are not the two stage type but the one stage type.

3. Heat-holding Stability of the Microneedles

If a microneedle array made of polyglycolic acid is put in 1,2-dichloroethane, the array sinks to a bottom. If carbon tetrachloride is added and mixed with 1,2-dichloroethane, then the microneedle array floats up. Density of a mixture of 1,2-dichloroethane and carbon tetrachloride in a state where the microneedle array did not float up nor become deposited was measured with a set of 7 densimeters (SOGO LABORATORY GLASS WORKS CO., LTD), and thereby the density was determined as density of the microneedle array.

Crystallinity X (%) was calculated by the following formula using the density $\rho$ (g/cm$^3$) of the microneedle array made of polyglycolic acid.

$$X=(1/\rho_a-1/\rho)/(1/\rho_a-1/\rho_c)*100$$

wherein, $\rho_a$ is density of polyglycolic acid with a crystallinity of 0% (=1.500 g/cm$^3$), and $\rho_c$ is density of polyglycolic acid with a crystallinity of 100% (=1.700 g/cm$^3$).

Changes of density and size after being held at 60° C. for 24 hours were measured to examine temporal stability of the microneedle array. FIG. 5 and FIG. 6 show photographs of the microneedle arrays according to Example 1 and Comparative Example 1after being left at 60° C. for 24 hours. Furthermore, the density and the crystallinity thereof are shown in Table 1. In Comparative Example 1 with low crystallinity, crystallization progressed and the density rose while being left, so it is understood that the microneedle array was accordingly abnormally deformed.

TABLE 1

Physical properties of microneedle arrays of Example 1 and Comparative Example 1 before and after heating

| sample name | density (g/cm$^3$) | | crystallinity (%) | |
|---|---|---|---|---|
| | before heating | after heating | before heating | after heating |
| Example 1 | 1.578 | 1.580 | 42.0 | 43.0 |
| Comparative Example 1 | 1.504 | 1.560 | 2.3 | 32.7 |

In Example 1 in which crystallization has progressed, the changes of density and crystallinity by heat-holding are both extremely low. In contrast, in Comparative Example 1 in which the crystallinity in molding is low, rises in density and crystallinity by heat-holding are remarkable. When the microscope photographs are compared, it is found that the shape does not almost change in Example 1 while contraction of the needles is remarkable in Comparative Example 1.

For each Example and Comparative Example, a tip height after the manufacture (A) and a tip height after being held at 60° C. for 24 hours (B) were compared. In Examples with high crystallinity, A and B are nearly same values (the needles do not contract). However, in Examples with low crystallinity, B is smaller than A, and thus the tips greatly contract. Table 2 shows the results.

4. Strength of the Microneedles

The microneedles should have sufficient strength to allow for insertion into skin. Since it is conceivable that microneedles with high compressive strength can be easily inserted into skin, the compressive strength of the microneedles was measured with a compact desk testing machine (Shimazu Corporation, EZTest). A sample was sandwiched by two stainless steel plates and compressed at rate of 1.0 mm/min to determine yield point stress. Yield point stress per one microneedle was determined as the compressive strength (Compressive strength=Yield point stress/Number of needles). FIG. 7 shows the results. The reference character 20 is the result of the microneedle array according to Example 1, 21 is the result of the microneedle array according to Comparative Example 1. The compressive strength is 0.07 N in Example 1 while a clear yield point is not shown in Comparative Example. Table 2 shows values of the compressive strength in all Examples and Comparative Examples. Since the yield point was not shown in Comparative Examples, the values are shown by (–).

The microneedles according to Example 3 and Comparative Example 3 were attached to substrate rear sides with adhesive tape and administered to an upper arm skin of a volunteer using an applicator. The microneedles just after the administration were collected and measured whether each microneedle had been bent by the skin administration. The number of the needles in one microneedle array was 458. A ratio of the bent needles was 1.1% in Example 3 while 80% of needles had been bent in Comparative Example 3. Microscope photographs are shown in FIG. 8 (Example 3) and FIG. 9 (Comparative Example 3).

When the needle tips to which model pigment had been applied were inserted into isolated human skin and then pulled out 30 minutes after administration, the pigment almost disappeared from the entire microneedles, so it was confirmed that the microneedles according to Example 3 were almost surely administered into the skin. Furthermore, the microneedles according to Example 3 were administered to an upper arm skin of a volunteer using the applicator, and then it was directly confirmed with OCT that the microneedles were inserted into deep parts of the skin.

A substrate rear side of the microneedle array according to Example 1 has unevenness. A depth of the concave parts is 0.3 mm, and the concave parts occupy 60% of the rear side (see FIG. 3). In order to confirm effect of the unevenness of the substrate, a microneedle array referred to as Example 9 which did not have the concave parts was made in a similar injection molding condition to Example 1. The microneedle arrays according to Example 1 and Example 9 were held at 40° C. for three months, and FIG. 11 and FIG. 12 show microscope photographs from a horizontal direction of the both arrays after being held. Warpage of the rear side of the microneedle array was not almost observed in Example 1 while warpage up to 0.32 mm was observed in Example 9 (distance between the arrowheads in FIG. 12=0.32 mm). Although a skin insertion property can be ensured even if the flatness of the microneedle array is somewhat disordered, it is desirable to be plane.

5. Conclusion

As described above, it is confirmed that the crystallization of the polyglycolic acid microneedles exerts serious influence on physical properties of the microneedle. A method in which degree of the crystallization can be most sensitively reflected and easily measured is to measure change of needle height of the microneedle array after being heated at 60° C. for 24 hours. Ratios (B/A) of a tip needle height (A) and a needle height (B) after being heated at 60° C. for 24 hours of the microneedle arrays made under various conditions are summarized as contraction rates (%) in Table 2. Although the microneedle arrays according to Example 8 and Comparative Example 4 were not the two step type but the one step type, there was little difference concerning the manufacturing conditions and the contraction rate between the two step type and the one step type.

The invention claimed is:

1. A microneedle array, wherein:
   polyglycolic acid is used as a material;
   crystallinity of the polyglycolic acid is 21% or more; and
   an axial contraction rate of tips is 99% or more.

2. The microneedle array according to claim 1, characterized in that the microneedle array has a yield point in compressive strength measurement.

3. The microneedle array according to claim 1, characterized in that:
   the microneedle has a conical, or circular truncated cone, or konide-like shape;
   the microneedle takes one stage structure or two stage structure;
   the needle height of the microneedle is 0.1-1.5 mm; and
   intervals between the microneedles are 0.2-1.5 mm.

4. The microneedle array according to claim 1, characterized in that an upper part of a substrate has a substrate base stand part, and/or a lower part of the substrate has unevenness.

5. The microneedle array according to claim 1, characterized in that:
   a concave part in the lower part of the substrate has a depth of 0.2 mm or more; and
   the concave parts occupy 10-90% of the entire substrate area.

6. The microneedle array according to claim 1, characterized in that a drug is held in the tips of the microneedles.

7. A manufacturing method of a microneedle array, wherein
   polyglycolic acid is injection-molded at a cylinder temperature of 230-280° C., a metal mold temperature of 60-130° C., and an injection pressure of 1000-1500 KPa, so as to manufacture the microneedle array in which crystallinity of the polyglycolic acid is 21% or more, and an axial contraction rate of tips is 99% or more.

8. A percutaneous absorption preparation, wherein
   a drug is held on a range of 500 μm from tips of a microneedle array
   in which polyglycolic acid, whose crystallinity is 21% or more and an axial contraction rate of tips is 99% or more, is used as a material.

9. The microneedle array according to claim 1, wherein the crystallinity of the polyglycol acid is 26.9% or more.

TABLE 2

Contraction rate of microneedles injection-molded under various conditions

| Examples Comparative Examples | cylinder temperature (° C.) | metal mold temperature (° C.) | crystallinity (%) | tip height of needle (A) (μm) | tip height of needle (B) (μm) | contraction rate (B/A) (%) | compressive strength (N/microneedle) |
|---|---|---|---|---|---|---|---|
| Ex. 1 | 235 | 120 | 42 | 294 | 292 | 99.3 | 0.070 |
| Ex. 2 | 235 | 105 | 36.3 | 292 | 291 | 99.7 | 0.077 |
| Ex. 3 | 235 | 95 | 33.7 | 293 | 292 | 99.7 | 0.076 |
| Ex. 4 | 235 | 85 | 26.9 | 289 | 289 | 100 | 0.069 |
| Ex. 5 | 235 | 80 | 21 | 291 | 289 | 99.3 | 0.071 |
| Ex. 6 | 235 | 70 | | 283 | 285 | 100.7 | 0.066 |
| Ex. 7 | 235 | 60 | | 265 | 270 | 101.9 | 0.066 |
| Ex. 8 | 235 | 120 | | 296 | 296 | 100 | 0.075 |
| Comp. Ex. 1 | 260 | 40 | 2.3 | 251 | 148 | 59 | — |
| Comp. Ex. 2 | 260 | 40 | | 264 | 154 | 58.3 | — |
| Comp. Ex. 3 | 235 | 50 | 18 | 237 | 212 | 89.5 | — |
| Comp. Ex. 4 | 235 | 40 | 16.1 | 231 | 148 | 64.1 | — |
| Comp. Ex. 5 | 260 | 40 | | 270 | 179 | 66.3 | — |

10. The manufacturing method of a microneedle array according to claim 7, wherein said metal mold temperature is 85° C. to 130° C. and the crystallinity of the polyglycol acid is 26.9% or more.

* * * * *